(12) United States Patent
Su et al.

(10) Patent No.: US 11,925,454 B2
(45) Date of Patent: Mar. 12, 2024

(54) RESPIRATORY FUNCTION TESTING SYSTEM AND RESPIRATORY FUNCTION TESTING METHOD THEREOF

(71) Applicants: Chia-Chi Su, New Taipei (TW); Hsiao-Pao Yen, New Taipei (TW); Pei-Ling Hsu, New Taipei (TW); Chia-Hung Chen, New Taipei (TW)

(72) Inventors: Chia-Chi Su, New Taipei (TW); Hsiao-Pao Yen, New Taipei (TW); Pei-Ling Hsu, New Taipei (TW); Chia-Hung Chen, New Taipei (TW)

( * ) Notice: Subject to any disclaimer, the term of this patent is extended or adjusted under 35 U.S.C. 154(b) by 762 days.

(21) Appl. No.: 17/062,846

(22) Filed: Oct. 5, 2020

(65) Prior Publication Data

US 2021/0015401 A1 Jan. 21, 2021

(51) Int. Cl.
| | |
|---|---|
| A61B 5/08 | (2006.01) |
| A61B 5/00 | (2006.01) |
| A61B 5/087 | (2006.01) |
| A61B 5/091 | (2006.01) |
| A61B 7/00 | (2006.01) |
| G10K 5/02 | (2006.01) |

(52) U.S. Cl.
CPC ............ *A61B 5/0803* (2013.01); *A61B 5/087* (2013.01); *A61B 5/0871* (2013.01); *A61B 5/091* (2013.01); *A61B 5/7203* (2013.01); *A61B 5/7278* (2013.01); *A61B 7/003* (2013.01); *G10K 5/02* (2013.01)

(58) Field of Classification Search
CPC ..... A61B 5/0803; A61B 5/087; A61B 5/0871; A61B 5/091; A61B 5/7203; A61B 5/7278; A61B 7/003; A61B 5/0826; G10K 5/02

See application file for complete search history.

(56) References Cited

U.S. PATENT DOCUMENTS

| | | |
|---|---|---|
| 2006/0107755 A1 | 5/2006 | Kuo et al. |
| 2011/0092839 A1 | 4/2011 | Alshaer et al. |
| 2012/0157857 A1 | 6/2012 | Abe et al. |
| 2013/0018274 A1 | 1/2013 | O'Neill |
| 2016/0106375 A1 | 4/2016 | Leydon |
| 2017/0042503 A1 | 2/2017 | Su et al. |

FOREIGN PATENT DOCUMENTS

EP 2283773 A1 2/2011

*Primary Examiner* — David J. McCrosky
(74) *Attorney, Agent, or Firm* — Locke Lord LLP; Tim Tingkang Xia, Esq.

(57) ABSTRACT

A respiratory function testing system includes an air transforming device, a sound reception device and an operation device. The air transforming device is configured to collect exhaled and/or inhaled air for a predetermined period and generate a wide frequency range sound signal according to the collected respired air. The wide frequency range sound signal at least contains an ultrasonic signal. The sound reception device is configured to receive and record the wide frequency range sound signal as an audio file. The operation device is in communication with the sound reception device and is configured to receive and compute the audio file to generate a respiratory function parameter. Besides, the recorded wide frequency range sound signal may be converted into a spectrogram for further applications, and the computation of the audio file can be replaced by analyzing the spectrogram. A respiratory function testing method corresponding to the respiratory function testing system is also provided.

18 Claims, 4 Drawing Sheets

RESPIRATORY FUNCTION TESTING SYSTEM AND RESPIRATORY FUNCTION TESTING METHOD THEREOF

CROSS REFERENCE

The present application is a continuation in part application of U.S. patent application Ser. No. 15/232,809, filed on Aug. 10, 2016; the content thereof is incorporated by reference herein.

FIELD OF THE INVENTION

The present invention relates to respiratory function testing system and respiratory function testing method thereof, and more particularly to respiratory function testing system and respiratory function testing method thereof utilizing ultrasonic signals generated by exhaled and/or inhaled air of a user.

BACKGROUND OF THE INVENTION

Current commercial spirometry on the market is mainly plastic pressure indicator based or turbine based. For a spirometry with plastic pressure indicator based, the pressure generated by the respiration flowing through the spirometry is for driving the sensor/receptor disposed at the end or side of the spirometry to generate a corresponding respiratory (e.g.; expiratory and/or inspiratory) signal. This type of spirometry has an uncomplicated structure, however, it is impossible to continuously monitor the respiratory signal within one respiratory period. For a spirometry with turbine based, the pressure generated by the respiration flowing through the spirometry is for driving the fan disposed in the spirometry to rotate. Though measuring the current generated by the rotating fans or using infrared technology, the cycles or speed of the rotations of the fans is counted, and therefore, data related to respiratory functions within one respiratory period is calculated based on the number or speed of the rotations of the fans. However, both the plastic pressure indicator based and the turbine based are not effectively and precisely enough. Also, both of them only can provide messages and applications related to the gas flow rate and flow volume through therein, but cannot provide more messages and more applications.

SUMMARY OF THE INVENTION

One objective of the present invention is to provide a respiratory function testing system, wherein the respiratory function testing technical adopted by the respiratory function testing system is different from the spirometry mentioned in BACKGROUND OF THE INVENTION.

Another objective of the present invention is to provide a respiratory function testing method applicable to the respiratory function testing system.

The present invention provides a respiratory function testing system, which includes an air transforming device, a sound reception device and an operation device. The air transforming device is configured to collect a respired (e.g.; exhaled and/or inhaled) air generated by an user for a predetermined period and generate a wide frequency range sound signal according to the collected respired air. The wide frequency range sound signal at least contains an ultrasonic signal, such as signal having frequency not smaller than 20 KHz. The sound reception device is configured to receive and record the wide frequency range sound signal. The operation device is in communication with the sound reception device and is configured to receive and compute the audio file (or viewed as computing these information contained in the audio file) to calculated respiratory function parameters.

The present invention provides a respiratory function testing method applicable to the above respiratory function testing system. The respiratory function testing method includes: collecting a respired air for a predetermined period and generating a wide frequency range sound signal according to the collected respired air, wherein the wide frequency range sound signal at least contains an ultrasonic signal; receiving and recording the wide frequency range sound signal as an audio file; and computing the audio file (or viewed as computing these information contained in the audio file) to generate corresponding respiratory function parameters.

Particularly, both the provided system and the provided method may convert the audio file a spectrogram (or viewed as the time-frequency diagram) and then analyze the spectrogram (or viewed as analyze these information converted from those information contained in the audio file). By analyzing the spectrogram instead of computing the audio file, not only the characters of the user's respiration may be identified, but also the background noise may be filtered out and also the user's privacy may be protected.

In summary, by sequentially configuring the air transforming device to collect exhaled and/or inhaled air for a predetermined period and generate a wide frequency range sound signal according to the collected respired air, configuring the sound reception device to receive and record the wide frequency range sound signal, and configuring the operation device to receive and compute these information contained in the wide frequency range sound signal to generate one or more respiratory function parameters, the respiratory function testing system and the respiratory function testing method of the present invention can determine whether a user has a normal respiratory function and acquire the user's respiratory function parameters values.

BRIEF DESCRIPTION OF THE DRAWINGS

Other advantages, objectives and features of the present invention will become apparent from the following description referring to the attached drawings.

DETAILED DESCRIPTION OF THE INVENTION

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
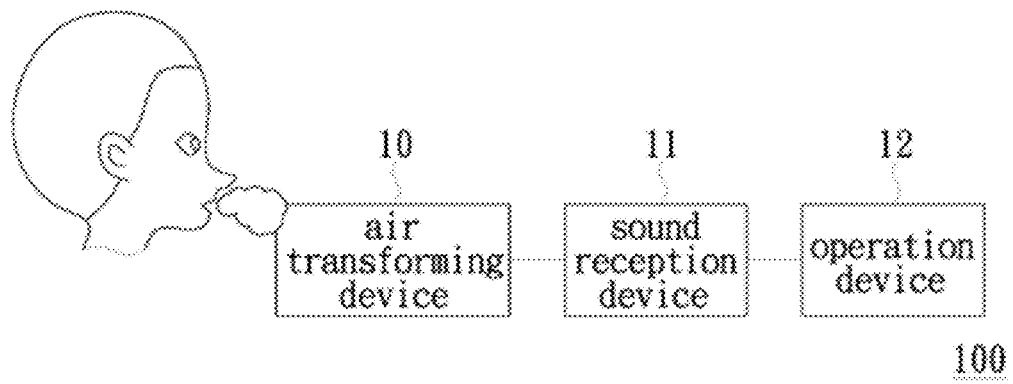
FIG. 1 is a schematic diagram of a respiratory function testing system in accordance with an embodiment of the present invention.

FIG. 1 is a schematic diagram of a respiratory function testing system in accordance with an embodiment of the present invention. As shown in FIG. 1, the respiratory function testing system 100 of the present embodiment includes an air transforming device 10, a sound reception device 11 and an operation device 12. The air transforming device 10 is configured to collect a respired air of a user for a predetermined period and generate a wide frequency range sound signal accordingly, wherein the wide frequency range sound signal at least contains an ultrasonic signal and some background sound may unavoidably collected during the predetermined period. In the present embodiment, the aforementioned predetermined period is, for example, the duration of a user continuously respiring, even only exhaling or inhaling, air through the air transforming device 10. The sound reception device 11 is configured to receive and record the wide frequency range sound signal generated by the air transforming device 10. In the present embodiment, the wide frequency range sound signal generated by the air transforming device 10 according to the respiration (inhalation and/or exhalation) of the user covers some of the frequency bands higher than 20 KHz. For example, the sound reception device 11 is configured to continuously receive and record the wide frequency range sound signal at a frequency higher than 20 KHz for the predetermined period. Although different users may have different durations of respiration due to the different respective respiratory functions, the respiratory function testing system 100 of the present invention is capable of testing the respiratory functions for the predetermined period for different users.

In the present embodiment, the sound reception device 11 is a microelectromechanical system (MEMS), a microphone, a smartphone or any equivalent device. Specifically, the sound reception device 11 is a highly-sensitive microphone capable of receiving and recording the wide frequency range sound signals and is selected from a group consisting of: omnidirectional microphone, cardioid microphone, hypercardioid microphone, shotgun microphone and bi-directional microphone. In addition, the highly-sensitive microphone may be integrated into a smartphone or a portable device so as to increase the use efficiency of the presented system. Because of having sensitive sound reception functions, each one of the microphones in the aforementioned group can be used to receive and record the wide frequency range sound signals and store the recorded wide frequency range sound signal as an audio file, wherein the audio length of the audio file is the aforementioned predetermined period. The operation device 12 has a communicating connection with the sound reception device 11. The operation device 12 is configured to receive and compute the information contained in the wide frequency range sound signal to generate at least one respiratory function parameter. In the present embodiment, the aforementioned communicating connection between the sound reception device 11 and the operation device 12 may be implemented via Bluetooth®, Wi-Fi, 4G, 5G or other available wireless means, though which the operation device 12 can receive the audio file from the sound reception device 11. In the present embodiment, the operation device 12 is an electronic device having computing capability such as a smart phone, a tablet or a laptop, and the present invention is not limited thereto.

In one embodiment, the air transforming device 10 includes one or more silent whistles or Galton's whistles (not shown). The silent whistle or Galton's whistle is configured to generate the ultrasound signal according to the exhaled and/or inhaled air while the user exhales air toward and/or inhales air through the air transforming device 10. The air transforming device 10 may include other types of ultrasound generator devices as long as such device is capable of generating the ultrasound signal according to the exhaled and/or inhaled air of the user, and the present invention is not limited thereto.

Figure 2:
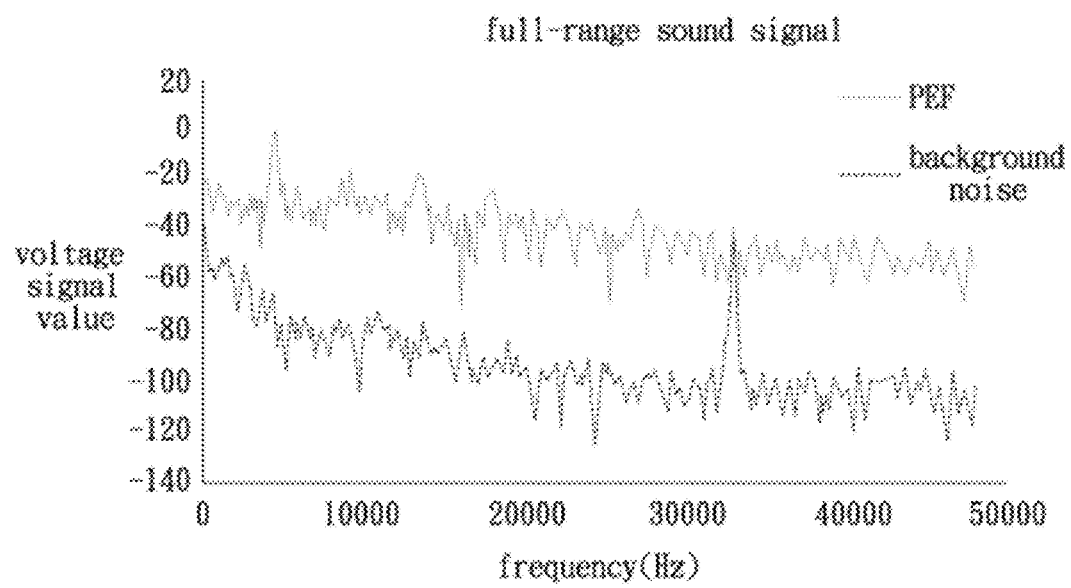
FIG. 2 is a schematic plot of wide frequency range sound signal verse time in accordance with an embodiment of the present invention.

FIG. 2 is a schematic plot of wide frequency range sound signal versus time in accordance with an embodiment of the present invention, wherein the wide frequency range sound signal is represented by voltage signal values. After the operation device 12 receives the audio file of the wide frequency range sound signal (FIG. 2) from the sound reception device 11, the user can select the wide frequency range sound signal at a specific frequency for computing via an application program installed in the operation device 12. The purpose of the frequency selection is for reducing the interference from background noise in the environment and thereby increasing the accuracy of the computation. Specifically, the operation device 12 is configured to capture the sound pressure corresponding to the wide frequency range sound signal at a predetermined frequency. The predetermined frequency may be determined by the application program automatically or set by the user. The aforementioned sound pressure is referred as the volume of the wide frequency range sound signal and measured in decibels (dB) or fast Fourier transform (FFT). The wide frequency range sound signal may have different sound pressures at different frequencies. Therefore, by a proper frequency selection, a qualifying computing result may still be obtained even if the user has a smaller amount of respiration.

Figure 3:
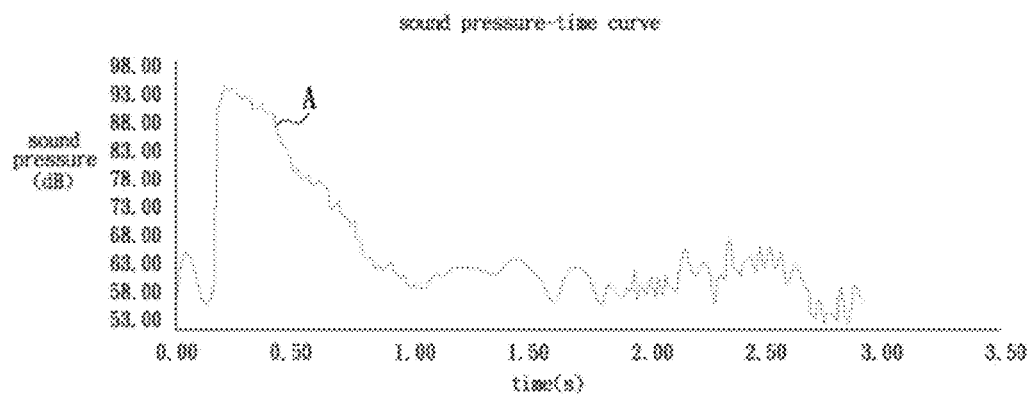
FIG. 3 is a schematic plot of sound pressure-time curve in accordance with an embodiment of the present invention.

FIG. 3 is a schematic plot of sound pressure-time curve in accordance with an embodiment of the present invention. In FIG. 3, the curve A presents the sound pressures corresponding to the exhalation of the user within 0-3 seconds once a specific frequency is selected by the operation device 12, wherein the horizontal axis represents the dimension of time (e.g., in seconds) and the vertical axis represents the dimension of sound pressure (e.g., in dB). Specifically, the operation device 12 is configured to perform a transforming operation on the audio file of the ultrasonic signal contained in the wide frequency range sound signal to generate the respiratory function parameter(s). Herein, these possible types of the respiratory function parameter include but are not limited to the peak expiratory flow (PEF−), the forced expiratory volume 1 (PEV1) and the forced vital capacity (FVC).

Figure 4:
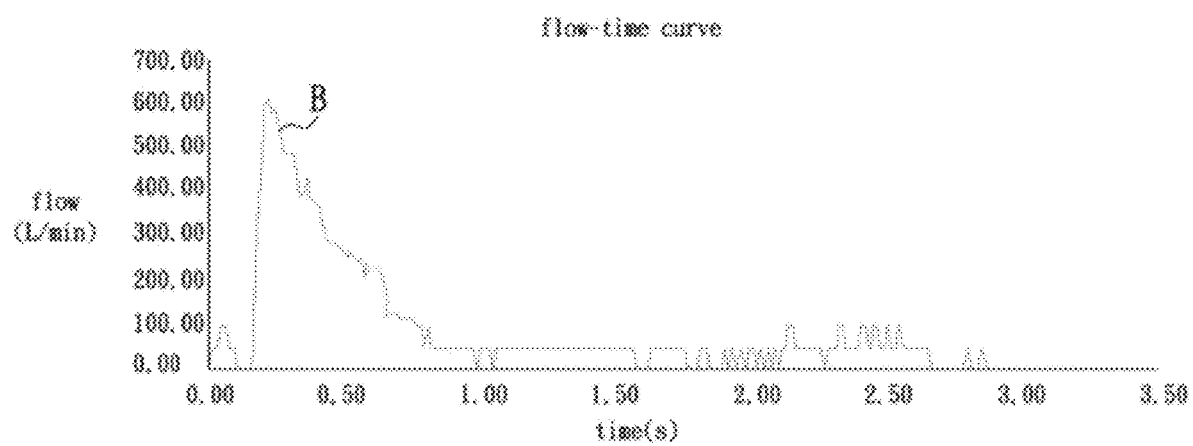
FIG. 4 is a schematic plot of flow-time curve in accordance with an embodiment of the present invention.

FIG. 4 is a schematic flow-time curve in accordance with an embodiment of the present invention, wherein the plot is transformed from FIG. 3 through a regression equation (e.g., a polynomial of one or more than one degrees such as y=ax+b, y=ax$^2$+bx+c). Specifically, the curve B in FIG. 4 is obtained by comparing the curve A in FIG. 3 with the regression equation and verified with the spirometry certified by the US Food and Drug Administration (FDA). In the regression equation, y stands a testing value derived from a spirometry certified by FDA and x stands a testing value derived from the respiratory function testing system 100 of the present embodiment. In FIG. 4, PEF is referred as the maximum value of the curve B within a predetermined period. Specifically, the PEF in FIG. 4 is 614.78 L/min and occurs at the point 0.22 in time.

Figure 5:
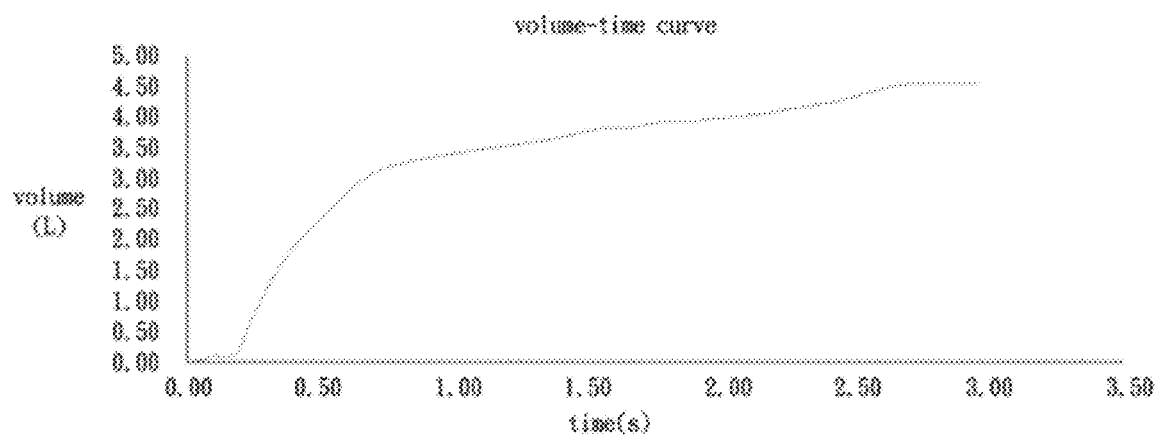
FIG. 5 is a schematic plot of volume-time curve in accordance with an embodiment of the present invention.

FIG. 5 is a schematic volume-time curve in accordance with an embodiment of the present invention, wherein the plot is transformed from FIG. 4. Specifically, the curve in FIG. 5 is obtained by performing the trapezoidal area integration formula on the curve B in FIG. 4 to accumulate the areas covered by the curve B. FEV 1 is referred as the volume of expiration in the first second. In FIG. 5, for example, FEV1 is the value of volume corresponding to the point 1 in time. Further, FVC is referred as the volume of expiration within 0-3 seconds. That is to say, FVC is referred as the volume of expiration within a predetermined period of one respiratory function test. In FIG. 5, for example, FVC is the value of volume corresponding to the point 3 in time.

After all of the PEF, FEV1 and FVC are calculated, the condition of the respiratory functions of the user can be determined through comparing the calculated PEF, FEV1 and FVC with respective determined standard values. In general, the standard value of PEF is higher than 80% and the standard value of ratio of FEV1 to FVC is higher than 70%. Therefore, for an asthma patient, it is determined that the patient has a proper treatment if the variation (%) of PEF is lower than 20%; it is determined that the patient may need to increase the amount of medicine if the variation of PEF is in a range between 20%-30%; and it is determined that the patient is having asthma and may need an emergency treatment if the variation of PEF is higher than 30%. Herein the variation (%) of PEF is referred as: ((the maximum PEF)−(the minimum PEF))/((the maximum PEF)+(the minimum PEF))*100%.

Figure 6:
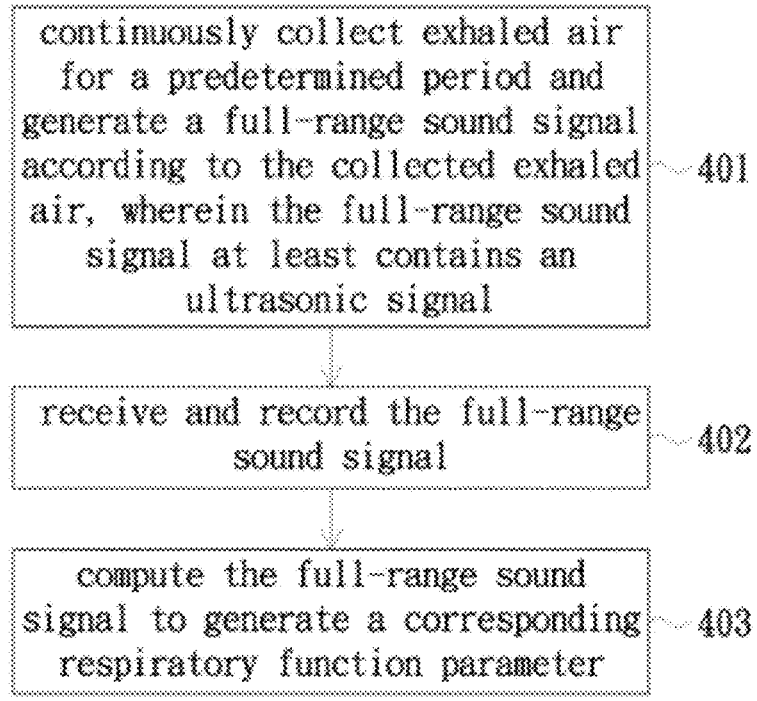
FIG. 6 is a flow chart of a respiratory function testing method in accordance with an embodiment of the present invention.

FIG. 6 is a flow chart of a respiratory function testing method in accordance with an embodiment of the present invention. As shown in FIG. 6, the respiratory function testing method of the present embodiment is applicable to the respiratory function testing system 100 and includes steps 401-403. Specifically, step 401: continuously collecting a respired air for a predetermined period and generating a wide frequency range sound signal according to the collected respired air, wherein the wide frequency range sound signal at least contains an ultrasonic signal. Step 402: receiving and recording the wide frequency range sound signal. Step 403: computing the wide frequency range sound signal to generate a corresponding respiratory function parameter.

Refer to Table 1, which is a comparison between the PEF derived from the respiratory function testing system of the present invention and PEF derived from the spirometry certified by FDA 9 hereunder is referred as a comparative example). As shown in Table 1, there are thirteen participants involved to the comparison. Specifically, each of the participants repeats the spirometric experiments three times for both of the systems of the present invention and the comparative example. The results of experiments indicate that all of the error rates of the system of the present invention relative to the comparative example are lower than 7%. Therefore, it is shown that the accuracy of the respiratory function testing system of the present invention is as good as that of the spirometry certified by FDA.

TABLE 1

Comparison of PEF between the Present Invention and Comparative Examples

| Participants | Gender | Age | Height (cm) | Comparative Examples PEF (L/min) | Present Invention PEF (L/min) | Error Rates |
|---|---|---|---|---|---|---|
| 1 | M | 23 | 167 | 619 | 657.57 | 6% |
| 2 | F | 10 | 140 | 286 | 277.68 | 3% |
| 3 | F | 30 | 159 | 341 | 346.88 | 2% |
| 4 | F | 28 | 153 | 375 | 355.99 | 5% |
| 5 | F | 28 | 153 | 356 | 344.20 | 3% |
| 6 | M | 40 | 176 | 618 | 614.91 | 1% |
| 7 | F | 46 | 156 | 367 | 364.68 | 1% |
| 8 | F | 28 | 153 | 366 | 356.29 | 3% |
| 9 | F | 28 | 153 | 380 | 361.81 | 5% |
| 10 | M | 40 | 176 | 622 | 615.76 | 1% |
| 11 | M | 58 | 168 | 545 | 554.91 | 2% |
| 12 | M | 40 | 176 | 588 | 629.67 | 7% |
| 13 | F | 28 | 153 | 365 | 374.77 | 3% |

In summary, by sequentially configuring the air transforming device to collect respired (e.g.; exhaled and/or inhaled) air for a predetermined period and generate a wide-frequency sound signal according to the collected exhaled and/or inhaled air, configuring the sound reception device to receive and record the wide frequency range sound signal and configuring the operation device to receive and compute the ultrasonic signal contained in the wide frequency range sound signal to generate a respiratory function parameter, the respiratory function testing system and the respiratory function testing method of the present invention can determine whether a user has a normal respiratory function.

Figure 7:
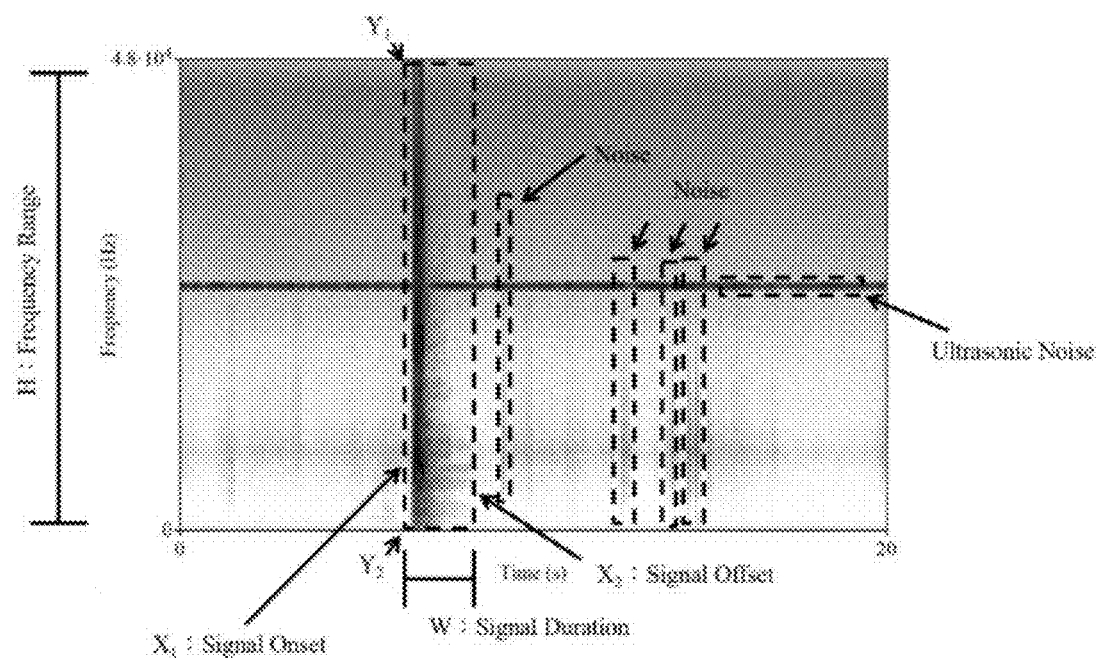
FIG. 7 is an exemplary spectrogram showing some popularly used labels.

Optionally, the operation device can have a built-in AI module to automatically analyze the spectrogram. For example, as shown in FIG. 7, to decide the Signal Onset X1 corresponding to the starting of a respiration signal, the Signal Offset X2 corresponding to the finishing of a respiration signal, the Signal Duration W corresponding to the duration of a respiration signal, the frequency range Y1/Y2 corresponding to terminals of the frequency range of a Signal. As well-known, the built-in AI module is trained by repeatedly collecting different respired air during different predetermined periods and comparing the different spectrograms with the respiration results decided by other current available methods. Again, the feature of this invention is using the AI module to analyze the spectrogram, but the details of such AI module is limited, i.e., any well-known, on-developing and/or to-be appeared AI module can be used herein.

Further, the analysis of the spectrogram may classify one or more signal by executing one or more of the following rules: (1) pick out any signal whose amplitude is not lower than an amplitude threshold, (2) pick out any signal whose duration is not shorter than a lower duration threshold, (3) pick out any signal whose duration is not longer than a higher duration threshold, and (4) pick out any signal whose frequency range is not shorted than a frequency threshold. The first rule can filter out weaker signals and then reduce the noise interference, the second rule can filter out shorter signal may not correspond a complete respiration wherein the lower duration threshold should be adjusted according to whether the user is a child, an adult or a patient, the third rule can reduce the waste of calculate outlier signals, and the fourth rule can take advantage of the wind-frequency sound signal where the spectrogram is converted from.

Moreover, the analysis of the spectrogram may classify one or more signal by executing one or more of the following rules: (1) pick out the first signal while two or more signals are appeared, (2) pick out two or more signals which are separated mutually, calculate the respiratory function parameters corresponding to each of these signals, and then use the largest value of the respiratory function parameter as the value of the user's respiratory function parameter; and (3) pick out two or more signals which are separated mutually, calculate the respiratory function parameters corresponding to each of these signals, and then use the average value of these calculated respiratory function parameters as the value of the user's respiration function parameter. The first rule can minimize any confusion induced by multiple respirations during the predetermined period. The second rule and the third rule are replaceable mutually, both of them can be used to calculate the user's respiration function parameter. As usual, which rule is used is depended on whose calculation speed via software is faster.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A respiratory function testing system, comprising:
   an air transforming device, configured to collect a user's respired air for a predetermined period and generate a wide-frequency sound signal according to the collected respired air, wherein the wide-frequency sound signal comprises an ultrasonic signal;
   a sound reception device, configured to receive and record the wide-frequency sound signal, and to store the recorded wide-frequency sound signal as an audio file; and
   an operation device, configured to communicate with the sound reception device and to receive the audio file;
   wherein the operation device is configured to convert the audio file into a spectrogram;
   wherein the operation device is configured to use a built-in AI module to decide automatically Signal Onset X1 of the spectrogram, Signal Offset X2 of the spectrogram, Signal Duration W of the spectrogram, and frequency range Y1/Y2 of the spectrogram, wherein the built-in AI module is trained by repeatedly collecting different respired air during different predetermined periods and comparing different spectrograms with respiration results.

2. The respiratory function testing system according to claim 1, wherein the operation device is configured to compute the ultrasonic signal at a predetermined frequency in the wide-frequency sound signal to generate a respiratory function parameter, wherein the operation device is configured to compute the ultrasonic signal by transforming a sound pressure of the ultrasonic signal under the predetermined period into a flow of the respired air under the predetermined period through a regression equation, and wherein the predetermined frequency is automatically determined by the operation device.

3. The respiratory function testing system according to claim 2, wherein the respiratory function parameter comprises peak expiratory flow (PEF), forced expiratory volume 1 (FEV1) and forced vital capacity (FVC).

4. The respiratory function testing system according to claim 2, wherein the operation device is further configured to capture the sound pressure corresponding to the wide-frequency sound signal at the predetermined frequency and the sound pressure corresponding to the predetermined frequency is adapted for reducing interference from a background noise.

5. The respiratory function testing system according to claim 4, wherein the operation device is configured to analyze the spectrogram for classifying a plurality of respiration classes of the user generating the respired air, and wherein the respiration classes comprise normal respiration, snore, apnea and deep respiring.

6. The respiratory function testing system according to claim 5, wherein the operation device is configured to analyze the spectrogram for distinguishing the background noise from any one of the respiration classes.

7. The respiratory function testing system according to claim 1, wherein the operation device is configured to classify one or more signals from the spectrogram by executing one or more of the following rules:
   picking out any signal whose amplitude is not lower than an amplitude threshold;
   picking out any signal whose duration is not shorter than a lower duration threshold;
   picking out any signal whose duration is not longer than a higher duration threshold; and
   picking out any signal whose frequency range is not shorter than a frequency threshold.

8. The respiratory function testing system according to claim 1, wherein the operation device is configured to analyze the spectrogram by using one or more of the following rules:
   picking out a first signal while two or more patterns are appeared; and
   picking out two or more patterns which are separated mutually, calculating a plurality of respiratory function parameters corresponding to each of these patterns, and then using the average value of these calculated respiratory function parameters as the value of the user's respiration function parameter.

9. The respiratory function testing system according to claim 1, wherein the operation device is configured to analyze the spectrogram by using one or more of the following rules:
   picking out a first signal while two or more patterns are appeared; and
   picking out two or more patterns which are separated mutually, calculating a plurality of respiratory function parameters corresponding to each of these patterns, and then using the largest value of the respiratory function parameter as the value of the user's respiratory function parameter.

10. A respiratory function testing method, comprising:
    collecting a respired air for a predetermined period and generating a wide-frequency sound signal according to the collected respired air, wherein the wide-frequency sound signal comprises an ultrasonic signal;
    receiving and recording the wide-frequency sound signal, and storing the recorded wide-frequency sound signal as an audio file;
    converting the audio file into a spectrogram; and
    using a built-in AI module to decide automatically Signal Onset X1 of the spectrogram, Signal Offset X2 of the spectrogram, Signal Duration W of the spectrogram, and frequency range Y1/Y2 of the spectrogram, wherein the built-in AI module is trained by repeatedly collecting different respired air during different predetermined periods and comparing different spectrograms with respiration results.

11. The respiratory function testing method according to claim 10, further comprising computing the ultrasonic signal at a predetermined frequency in the wide-frequency sound signal from the audio file to generate a corresponding respiratory function parameter, wherein to compute the ultrasonic signal comprises transforming a sound pressure of the ultrasonic signal under the predetermined period into a flow of the respired air under the predetermined period through a regression equation, wherein the predetermined frequency is automatically determined by the operation device.

12. The respiratory function testing method according to claim 11, wherein the respiratory function parameter comprises peak expiratory flow (PEF), forced expiratory volume 1 (FEV1) and forced vital capacity (FVC).

13. The respiratory function testing method according to claim 11, further comprising:
    capturing the sound pressure corresponding to the wide-frequency sound signal at the predetermined frequency, wherein the sound pressure corresponding to the predetermined frequency is adapted for reducing interference from a background noise.

14. The respiratory function testing method according to claim 13, further comprising analyzing the spectrogram for classifying a plurality of respiration classes of the user generating the respired air, wherein the respiration classes comprise normal respiration, snore, apnea and deep respiring.

15. The respiratory function testing method according to claim 14, further comprising analyzing the spectrogram for distinguishing the background noise from any one of the respiration classes.

16. The respiratory function testing method according to claim 10, further comprising classifying one or more signals from the spectrogram by executing one or more of the following rules:
    picking out any signal whose amplitude is not lower than an amplitude threshold;
    picking out any signal whose duration is not shorter than a lower duration threshold;
    picking out any signal whose duration is not longer than a higher duration threshold; and
    picking out any signal whose frequency range is not shorter than a frequency threshold.

17. The respiratory function testing method according to claim 10, further comprising analyzing the spectrogram by using one or more of the following rules:
    picking out a first signal while two or more patterns are appeared; and
    picking out two or more patterns which are separated mutually, calculating a plurality of respiratory function parameters corresponding to each of these patterns, and then using the average value of these calculated respiratory function parameters as the value of the user's respiration function parameter.

18. The respiratory function testing method according to claim 10, further comprising analyzing the spectrogram by using one or more of the following rules:
    picking out a first signal while two or more patterns are appeared; and
    picking out two or more patterns which are separated mutually, calculating a plurality of respiratory function parameters corresponding to each of these patterns, and then using the largest value of the respiratory function parameter as the value of the user's respiratory function parameter.

* * * * *